(12) United States Patent
Huang et al.

(10) Patent No.: US 6,355,475 B1
(45) Date of Patent: Mar. 12, 2002

(54) ISOLATE OF ANTRODIA CAMPHORATA, PROCESS FOR PRODUCING A CULTURE OF THE SAME AND PRODUCT OBTAINED THEREBY

(75) Inventors: Ren-Chang Huang, Hualien Hsien; Jian-Chyi Chen, Miaoli Hsien; Bor-Cheh Wang, Hsinchu, all of (TW)

(73) Assignee: Council of Agriculture, Executive Yuan, Taipei (TW)

( * ) Notice: Subject to any disclaimer, the term of this patent is extended or adjusted under 35 U.S.C. 154(b) by 0 days.

(21) Appl. No.: 09/692,270

(22) Filed: Oct. 19, 2000

Related U.S. Application Data (62) Division of application No. 09/566,834, filed on May 8, 2000.

(30) Foreign Application Priority Data

Feb. 17, 2000 (TW) .......................................... 89102716
Feb. 18, 2000 (CN) .......................................... 00102365

(51) Int. Cl.[7] .............................. C12N 1/16; C12N 1/14
(52) U.S. Cl. ................................. 435/256.8; 435/254.1
(58) Field of Search ............................ 435/254.1, 256.8

(56) References Cited

PUBLICATIONS

Wu, S.H. Ryvarden L. and Chang, T.T. 1997 Antrodia camphorata ("niu–chang–chih"), new combination of a medicinal fungus in Taiwan. Bot. Bull. Acad. Sinica 38:273–275, Oct. 1997.*

* cited by examiner

*Primary Examiner*—Herbert J. Lilling
(74) *Attorney, Agent, or Firm*—Fish & Richardson P.C.

(57) ABSTRACT

The present invention relates a process for culturing isolates of *Antrodia camphorata* to provide a product useful in medical and nourishment fields. The present invention also relates to a novel isolate of *Antrodia camphorata* capable of growing in a suitable artificial medium, while exhibiting desired pharmacological activities, in particular anti-tumor activity. The utilization of potato dextrose broth and the synthetic medium containing fructose as major carbon source leads to a significant increase in the pharmacological activity of the cultures of *A. camphorata*.

6 Claims, 5 Drawing Sheets

ISOLATE OF ANTRODIA CAMPHORATA, PROCESS FOR PRODUCING A CULTURE OF THE SAME AND PRODUCT OBTAINED THEREBY

CROSS REFERENCES

This application is a divisional of U.S. Ser. No. 09/566,834, filed May 8, 2000, now pending.

FIELD OF THE INVENTION

The present invention relates a process for culturing isolates of *Antrodia camphorata* to provide a product useful in medical and nourishment fields. The present invention also relates to a novel isolate of *Antrodia camphorata*, the culture of which exhibits pharmacological activities when the isolate is grown in a suitable medium.

DESCRIPTION OF THE RELATED ART

*Antrodia camphorata* [(Zang & Su) S.-H. Wu, Ryvarden & T. T. Chang], also known as "niu-chang-chih" or "niu-chang-ku" in Taiwan, was recently reported as a new fungus species characterized by the cylindrical shape of its basidiospores appearing in fruit bodies, weakly amyloid skeletal hyphae, bitter taste and light cinnamon resupinate to pileate basidiocarps, as well as chlamydospores and anthroconidia in pure culture. The growth of this new fungus species is extremely slow and restricted to an endemic tree species, *Cinnamomum kanehirai* Hay (Lauraceae), as the only host. The detailed characterization and taxonomic position of *A. camphorate* were described in Chang, T. T. et al., *Antrodia cinnamomea* sp. nov. on *Cinnamomum kanehira* in Taiwan, Mycol. Res. 99(6): 756–758 (1995) and Wu, S.-H., et al., *Antrodia cinnamomea* ("niu-chang-chih"), New combination of a medicinal fungus in Taiwan, Bot. Bull. Acad. Sin. 38: 273–275 (1997), the entire disclosure of which is incorporated herein by reference.

In Taiwanese folk medicine, the fruit bodies of *A. camphorate* are believed to have certain medical effects. According to the traditional way, the fruit bodies are ground into dry powder or stewed with other herbal drugs for oral uptake to treat conditions caused by poisoning, diarrhea, abdominal pain, hypertension, skin itches and liver cancer. However, no pharmacological or clinical study in these aspects has appeared in literature to date. Because of the stringent host specificity and rarity in nature, as well as the failure of artificial cultivation, "niu-chang-chih" is very expensive in Taiwan. In recent years, the fruit bodies of this fungus with high quality have been sold at an extremely high price of around US $15,000 per kg.

Accordingly, there exists a need to establish a method for the large-scale cultivation of the fungus *A. camphorata* in a suitable artificial environment, while maintaining the pharmacological activities of the fungus *A. camphorata*. There also exists a need to obtain an isolate of *A. camphorata* that exhibits pharmaceutically useful activities when cultivated in a suitable artificial environment.

SUMMARY OF THE INVENTION

Accordingly, an object of the present invention is to provide a process suitable for culturing isolates of *A. camphorata*, which can grow well in the mycelial state when subjected to submerged fermentation. For this purpose, we have tested five isolates of *A. camphorata* collected in the Food Industry Research and Development Institute (FIRDI), Hsin-Chu, Taiwan, R.O.C. In addition, it is surprising to find that the culture of an obtained isolate exhibits a desired pharmacological activity, in particular an anti-tumor activity. According to a preferred embodiment of this invention, the carbon source of the medium, usually a carbohydrate, may be critical to obtain an optimized environment for culturing *A. camphorata*.

Another object of the present invention is to provide a novel isolate of *Antrodia camphorate* bearing a desired pharmacological activity, in particular an anti-tumor activity, when grown in a suitable artificial environment. For this purpose, we have isolated and identified an isolate of *A. camphorate*, which can grow well in the mycelial state when subjected to submerged fermentation, and the resulting culture exhibits excellent pharmacological activities.

The present invention thus provides a process for producing a culture of an isolate of *A. camphorata* having pharmacological activity, comprising the steps of:

(a) inoculating a mycelial inoculum of an isolate of *A. camphorata* into a medium suitable for the growth of said isolate;

(b) cultivating the resulting culture from step (a); and (c) harvesting the culture when the culture has a redness index a≧3 as measured using Hunter's coordinate system.

A still another object of the present invention is to provide a product obtained from the above process.

A further object of the present invention is to provide a pharmaceutical composition or a nutrient supplement containing a product obtained from the above process.

BRIEF DESCRIPTION OF THE DRAWINGS

The above and other objects and features of the present invention will become apparent with reference to the following description of the preferred embodiments taken in conjunction with the accompanying drawings, in which.

DETAILED DESCRIPTION OF THE INVENTION

In accordance with the present invention, one isolate of *A. camphorata* was isolated from Taitung County, Taiwan, R.O.C., and this and other four isolates of *A. camphorate* were successfully cultivated in a natural source medium or a synthetic medium. These five isolates were deposited in the Culture Collection and Research Center (CCRC) of the Food Industry Research and Development Institute (FIRDI), Hsinchu, Taiwan, R.O.C. under accession numbers CCRC 35396 (on Dec. 1, 1994), 35398 (on Dec. 1, 1994), 36401, 36795 and 930032 (on Jan. 27, 2000), respectively.

The term "natural medium" as used herein takes on its common meaning to a person skilled in the art and is directed to a medium mainly consisting of naturally occurring materials. According to the present invention, the commercially available potato dextrose broth from GIBCO is preferred.

The term "synthetic medium" as used herein is directed to an artificial mixture of various ingredients with defined chemical structures and optionally one or more crude ingredients derived from natural materials. In general, a synthetic medium comprises a carbon source, a nitrogen source, trace elements such as an inorganic salt, and optionally vitamins or other growth factors.

The carbon source includes but is not limited to glucose, sucrose, galactose, fructose, corn starch, malt extract and combinations thereof. From the view point of the intended effects, the synthetic medium preferably contains fructose as a major carbon source, and optionally supplemented with malt extract or glucose. Preferably, the carbon source is present in the range between 1.5–2.5% by weight, and more preferably in an amount of 2.5% by weight, on the basis of the total volume of the synthetic medium.

The nitrogen source includes but is not limited to ammonium sulfate, ammonium nitrate, sodium nitrate, casamino acid, yeast extract, peptone, tryptone and combinations thereof. Preferably, according to the present invention, the synthetic medium contains yeast extract as the nitrogen source. The nitrogen source is preferably present in the range between 0.2–2.0% by weight, and more preferably in an amount of 0.5% by weight, on the basis of the total volume of the synthetic medium.

The process of the present invention apparently has advantages of easy manipulation and ready access to the large-scale production of the desired fungus in the pharmaceutics industry, as compared with the traditional method of manipulating "niu-chang-chih," such as grounding and stewing the fruit bodies of the fungus per se.

The five isolates of *A. camphorata* were tested for their potential in the medical field, in particular their ability to inhibit the growth of tumor or cancer cells. To evaluate the competence of these isolates in inhibiting the growth of tumor cells, the aqueous phases of *A. camphorata* cultures in the natural and synthetic media were subjected to an MTT calorimetric assay.

The term "MTT calorimetric assay" or "MTT-tetrazolium assay" as used herein is directed to an anticancer drug screening scheme established in the 1980s by the U.S. National Cancer Institute's Developmental Therapeutics Program, Division of Cancer Treatment (see, for example, Alley, M. C., et al., Feasibility of drug screening with panels of human tumor cell lines using a microculture tetrazolium assay Cancer Res. 48: 589–601, 1988; Scudiero, D. A., et al., Evaluation of a soluble tetrazolium/formazan assay for cell growth and drug sensitivity in culture using human and other tumor cell lines. *Cancer Res*. 48: 4827–4833, 1988; Vistica, D. T., et al., Tetrazolium-based assays for cellular viability: a critical examination of selected parameters affecting formazan. *Cancer Res*. 51: 2515–2520, 1991; and Monks, A., et al., Feasibility of a high-flux anticancer drug screen using a diverse panel of cultured human tumor cell lines. *J. Nat. Cancer Inst*. 83: 757–766, 1991).

In the assay, potential anticancer drugs or natural products derived from plants or microbes (in this case, from the five isolates of *A. camphorate*) were tested for their ability against groups of cell line panels each representing a major clinical category of hum2n malignancy. The viable cell numbers per well are directly proportional to the production of formazan, which can be measured spectrophotometrically through solubilization. In principle, biologically active substances or natural products containing the substances can inhibit or even stop cell growth, and little formazan is formed consequently.

Amongst the five isolates, *A. camphorate* CCRC 930032, also deposited at the American Type Culture Center (ATCC) with accession no. PTA-1233 on Jan. 27, 2000 under the terms of the Budapest Treaty on the International Recognition of the Deposit of Microorganism for the Purpose of Patent Procedure, is found to have excellent pharmacological activity. In particular, the results from the MTT calorimetric assay reveal that *A. camphorate* CCRC 930032 when grown in the designed culture conditions (in potato dextrose broth or the synthetic medium containing fructose as the major carbon source) possesses excellent anti-tumor activities.

In view of our success of cultivating *A. camphorate* CCRC 930032 using the selected media, it will be appreciated by those skilled in the art that new isolates of *A. camphorata* having pharmacological activity characteristics substantially identical to those of *A. camphorate* CCRC 930032 can be isolated and cultivated using the present method described above.

Presumably, the unknown active substance(s) functioning to the target tumor cells are produced and secreted from the mycelium into the liquid phase of the culture if a suitable environment, such as the specific compositions in the medium, is given. Accordingly, our unexpected finding suggests a feasible process for large-scale production of *A. camphorata* by the optimized scale-up fermentation and a utilization of the cultures derived therefrom to manufacture useful materials, such as healthy food.

The present invention is therefore beneficial to the susceptibility of *A. camphorata* to herbal medicine applications. The present invention also opens a gate to utilization of the obtained *A. camphorata* culture in the treatment of cancer or tumor diseases in a patient in need of such treatment.

PREFERRED EMBODIMENTS FOR PRACTICING THE INVENTION

The following Examples are given for the purpose of illustration only and are not intended to limit the scope of the present invention.

EXAMPLE 1

Preparation of Liquid Cultures of *A. camphorata* CCRC 930032 in Natural Media

Maintenance of culture

The stock culture *A. camphorata* isolate CCRC 930032, which is deposited in the Culture Collection and Research Center (CCRC), was maintained with slant tubes of potato dextrose agar (PDA, purchased from Difco) at 25° C. and sub-cultured every two months. Working cultures on PDA plates were inoculated from PDA slants and incubated at 28° C. from 15 to 20 days.

Preparation of mycelial inoculum After an incubation period from 15 to 20 days, the mycelial characteristics of *Antrodia camphorate* CCRC 930032 were investigated under a light microscope to assure that no contamination occurred. The whole mycelia was cut into small pieces and then homogenized aseptically with 50 ml of sterile water in a homogenizer (Osterizer) for 30 seconds. 10 ml aliquots of the mycelial suspension were used as inoculum for the subsequent experiment.

Submerged shake culture

Potato dextrose broth (PDB, purchased from Difco) was prepared according to the instructions provided by the manufacturer. To 100 ml of the natural source medium in 500ml Erlenmeyer flasks, 10 ml inoculum of *A. camphorate* CCRC 930032 was added. The submerged cultures were incubated at 30° C. for 14 days with constant agitation (at 50 rpm on an orbital rotary shaker purchased from Hotech). At the end of incubation, the fungus cultures were passed through a simple filtration assembly of a suction filter funnel, a flask and a vacuum machine. The filtrates were used for the subsequent MTT colorimetric assay. The pellets harvested on the funnel were baked at 60° C. for 7 days, and the dry weights of the total cell mass were calculated. The experiment was triplicated.

Example 2

Preparation of Liquid Cultures of *A. camphorate* CCRC 930032 in Synthetic Media Example 1 was repeated except that the natural medium was replaced with synthetic media, each containing 0.5% (w/v) of yeast extract (Difco), 0.1% (w/v) of $KH_2PO_4$ (Merck), 0.05% (w/v) of $MgSO_4 \cdot 7H_2O$ (Merck) and 2.5% of a selected carbohydrate, i.e., fructose, glucose, sucrose, malt extract or corn starch, as the major carbon source. The experiment was also triplicated.

The results of Examples 1 and 2 are shown in Table 1.

TABLE 1

Dry weight of mycelium of *A. camphorata* CCRC 930032 grown in different culture media (fixed culture condition: 30° C., 50 rpm, and incubation for 14 days.)

| Culture medium | Dry weight of mycelium (g/L) | Color of broth |
| --- | --- | --- |
| Potato dextrose broth: 2.4 grams suspended in 100 ml distilled water | 2.776 | deep dark red |
| Synthetic medium: 0.5% yeast extract (Difco), 0.1% $KH_2PO_4$ (Merck), and 0.05% $MgSO_4 \cdot 7H_2O$ (Merck) matched with 2.5% of different carbon sources: | | |
| (1) fructose | 3.526 | dark red |
| (2) glucose | 3.661 | yellow |
| (3) malt extract | 5.02 | brown |
| (4) corn starch | 5.384 | pale yellow |

As shown in Table 1, the mycelia of the highest dry weights were obtained in the synthetic media with corn starch or malt extract as a carbon source. The average sizes of the mycelial pellets were fairly small, usually about 1–3 mm in diameter. The colors of the resultant cultures were variable and seem to depend upon the compositions included therein. For instance, the cultures obtained from potato dextrose broth appeared deep dark red in color, and a similar color was observed in the cultures derived from the synthetic medium added with fructose as the major carbon source. On the other hand, the colors shown in the rest of the cultures look quite different. The cultures resulting from the synthetic medium with glucose or corn starch as a carbon source turned yellow at the end of incubation, whereas the color of the cultures originating from the synthetic medium with malt extract was brown.

EXAMPLE 3

MTT (3-(4,5-dimethylthiazol-2-yl)-2,5-diphenyltetrazolium bromide) Colorimetric Assay Preparation of samples for MTT assay The culture filtrates of *A. camphorata* collected in Examples 1 and 2 (experimental samples) and the non-inoculated media (control samples) were used for MTT assay. The culture filtrates and media were adjusted with $NH_4OH$ to pH 7 and sterilized by autoclaving. The resultant samples were preserved at 4° C. before analysis.

Cell lines and culture

Tumor cell lines, including MCF-7, Hela, AGS, COLO 320HSR, and Hep G2 cells, etc., were selected for MTT calorimetric assay. They were maintained as stocks in RPMI 1640 (GIBCO BRL) supplemented with 10% fetal bovine serum (Hyclone) and 2mM L-glutamate (GIBCO BRL). The cultures of these cell lines were passaged once or twice weekly using trypsin-EDTA (GIBCO BRL) to detach the cells from cell culture flasks.

MTT-microculture tetrazolium assay

Tumor cells were harvested, counted and inoculated into a 96-well microtiter plate at the appropriate concentrations. For example, the start-up concentration of Hela cells was 1000 cells per well, and those of Hep3B2. 1-7, HepG2, AGS, COLO 320HSR and MCF-7 cells were 3000 cells per well. The total volume of the cell culture medium in each well was made up to 180 $\mu l$, and an incubation was carried out overnight at 37° C. in an incubator containing 5% $CO_2$.

20 $\mu l$ aliquots of the samples were applied to the culture wells intriplicate, and the resultant cultures were incubated for 3 days in the above-mentioned incubation condition. Subsequently, 20 $\mu l$ of MTT (Merck), prepared previously at 5 mg/ml in PBS solution (GIBCO BRL) and stored at 4° C., were added to each well.

After an additional 4-hour incubation at 37° C., the supernatant was removed from each well, and 100 $\mu l$ of 100% DMSO (dimethyl sulfoxide, available from Sigma) were added, in order to solubilize the MTT-formazan product. After thorough mixing with a mechanical plate mixer, absorbance at 540 nm was measured with a microplate reader (MRX, Dynex). The tumor cell growth inhibition rates of the tested culture filtrates of *A. camphorata* were calculated by dividing the absorbance of each experimental sample by that of the corresponding control sample. The results are shown in FIGS. 1 and 2.

Figure 1:
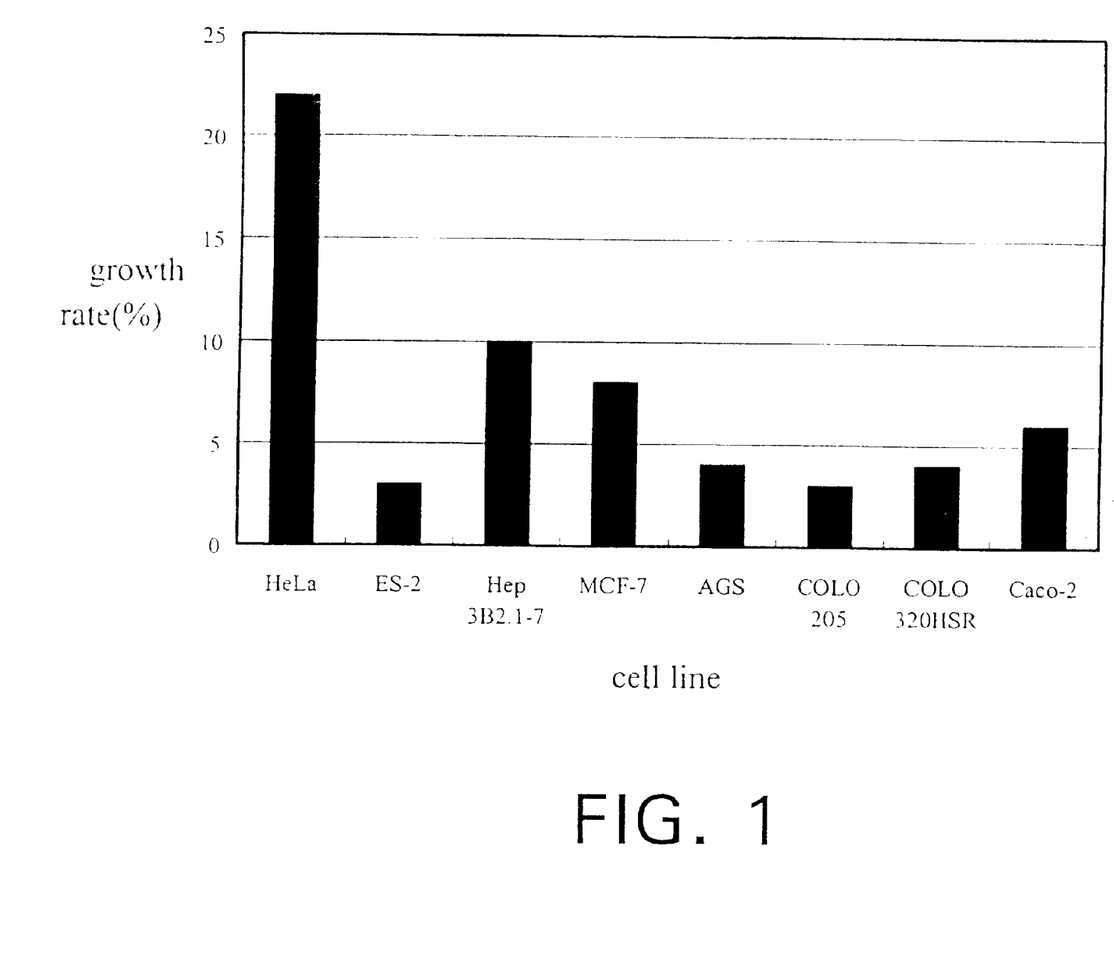
FIG. 1 is a diagram demonstrating the growth of tumor cells affected by the culture filtrate derived from a shake culture of *A. camphorata* CCRC 930032 in potato dextrose broth, in which the tested cell lines include Hela, ES-2, Hep 3B, MCF-7, AGS, COLO 205, COLO 320HSR, and Caco-2.

In FIG. 1, the selected culture medium is potato dextrose broth, and the incubation of *A. camphorata* isolate CCRC 930032 was conducted at 30° C., 50rpm, 10% inoculation volume for 14 days (Example 1). A culture filtrate was harvested from the culture and was incubated and tested in an MTT-tetrazolium assay against several typical tumor cell lines, including Hela, ES2, Hep3B, MCF-7, AGS, COLO 205, COLO 320HSR and Caco-2 cells.

FIG. 1 shows that the growth rates of the tumor cell lines are remarkably reduced by the addition of the culture filtrate from *A. camphorata* isolate CCRC 930032 in potato dextrose broth, as compared to the results from the control samples. For instance, the MCF-7 cells treated with the culture filtrate of Example 1 has a growth rate of 8% based on the growth rate of its counterpart control, whereas the COLO 320HSR and AGS cells so treated have a growth rate of only 4%.

Figure 2:
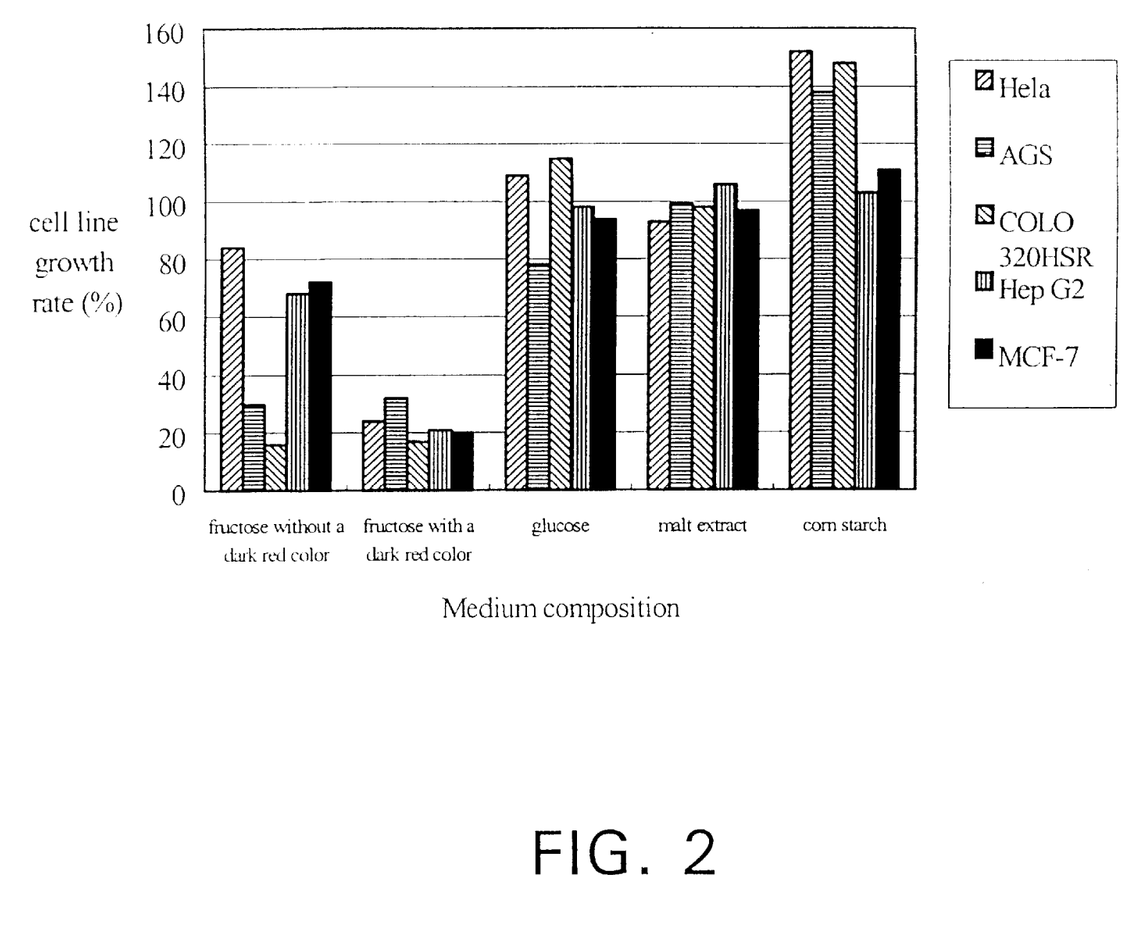
FIG. 2 is a diagram demonstrating the growth of tumor cells affected by the culture filtrates derived from shake cultures of *A. camphorate* CCRC 930032 in synthetic media, in which the tested cell lines include Hela, AGS, COLO 320HSR, Hep G2 and MCF-7 cells.

In FIG. 2, the synthetic medium composition as listed in Table 1 were employed, and the incubation lasted for 14 days at 30° C., 50 rpm, 10% inoculation volume. Five tumor cell lines, including Hela, MCF-7, AGS, COLO 320HSR and MCF-7 cells, were used for the MTT-tetrazolium assay. As shown in FIG. 2, a significant inhibitory effect on the growth of the tumor cells was observed in the cells treated with the culture filtrates from the synthetic media having fructose as the major carbon source. In addition, the growth rates were reduced to below 20% in COLO 320HSR and MCF-7 cell lines. Surprisingly, *A. camphorate* isolate CCRC 930032 does not significantly inhibit the growth of the tumor cell lines when cultured in the same synthetic medium having glucose, malt extract and corn starch as the major carbon source, respectively. Moreover, the inhibitory ability of *A. camphorata* isolate CCRC 930032 was reduced dramatically and was restricted to AGS and MCF-7 tumor cell lines when the culture medium, for certain reasons, sometimes fails to show a dark red color.

Accordingly, the dark red appearance of the culture filtrates from the potato dextrose broth and the synthetic medium containing fructose suggests that the observed inhibitory effects of the tested fungus cultures on the tumor cells are possibly correlated with the color of the culture. This presumption is further investigated in Example 4.

EXAMPLE 4

Figure 3:
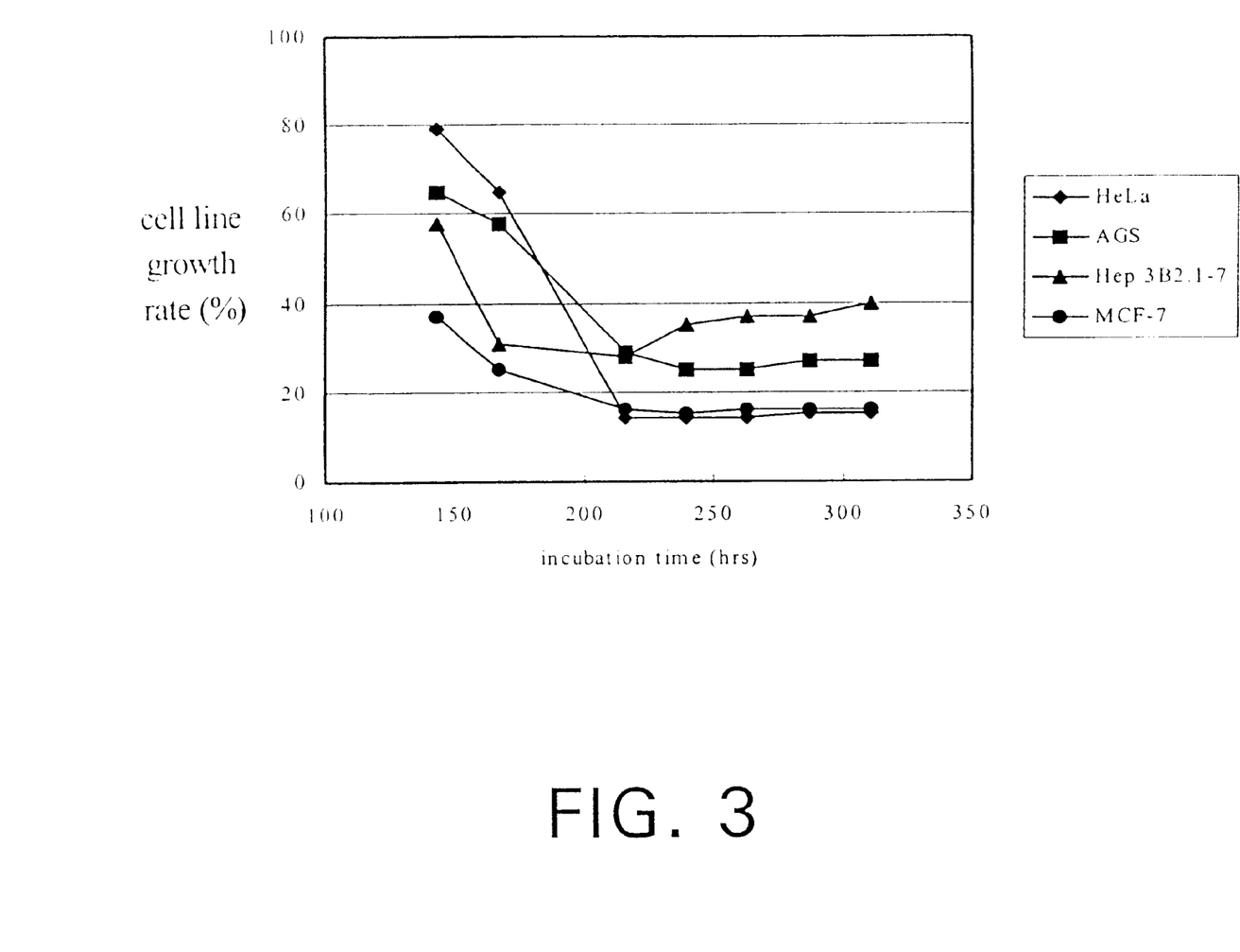
FIG. 3 is a diagram demonstrating the inhibiting effect of the shake culture filtrates of *A. camphorate* CCRC 930032 harvested at different sampling time points on the growth of tumor cells, in which the tested cell lines include Hela, AGS, Hep 3B2.1-7, and MCF-7 cells.

Coincidence of the Inhibitory Activity and Color Appearance of *A. camphorata* Filtrates In this example, the isolate CCRC 930032 was cultured in a 5-liter fermenter. Samples were removed from the culture at the 143rd, 167th, 216th, 239th, 263rd, 287th and 311st hours after the inoculation and were used for MTT-tetrazolium assay. The collected culture samples were detected with a Lovibond Tintometer PFX990, and the color appearances of the samples are represented by the "L," "a" and "b" coordinates in Hunter's coordinate system, in which a larger "L" value refers to a higher level of brightness, a more positive "a" value refers to a higher level of redness and a more positive "b" value refers to a higher level of yellowness. The start-up medium was used as a blank standard. The results are shown in FIG. 3 and Table 2 below.

TABLE 2

The tintometric analysis of the filtrate samples of *A. camphorata* CCRC 930032 picked up at the 143rd, 167th, 216th, 239th, 263rd, 287th, and 311st hours after the mycelial inoculation.

| Sampling Time (hour) | L | a | b |
|---|---|---|---|
| 143 | 63.12 | 3.71 | 18.03 |
| 167 | 79.09 | 4.04 | 20.56 |
| 216 | 76.04 | 8.62 | 25.60 |
| 239 | 76.50 | 10.67 | 24.34 |
| 163 | 75.34 | 12.91 | 27.30 |
| 187 | 74.47 | 13.94 | 29.74 |
| 311 | 73.26 | 14.94 | 33.42 |

It can be seen that the growth rates of the tumor cells drop significantly as the "a" values (i.e., the redness) of the filtrates increase abruptly. While a 20% inhibition against the tested tumor cells is shown when the "a" value of the culture filtrate is above 3, it is estimated by interpolation that the desired filtrates, i.e., the filtrates with a higher inhibitory effect on tumor cells, have an "a" value above 7 where the redness can be observed with bare eyes.

Without wishing to be limited by theory, it is presumed that the isolate CCRC 930032 may have an advantageous genetic background and therefore comprises, for example, a set of enzymes, which facilitate the production and/or the secretion of the active substance(s) in particular culture media. The metabolites, together with the environment of the medium, result in the color change of cultures from yellow to dark red. Perhaps, the active substances per se contain conjugated double bonds, such as terpenoids, and thus impart a dark red color to the liquid cultures to which they are secreted. Accordingly, the color appearance of the cultures may be a useful indicator for assessing the inhibitory activity of the culture.

EXAMPLE 5

Figure 4:
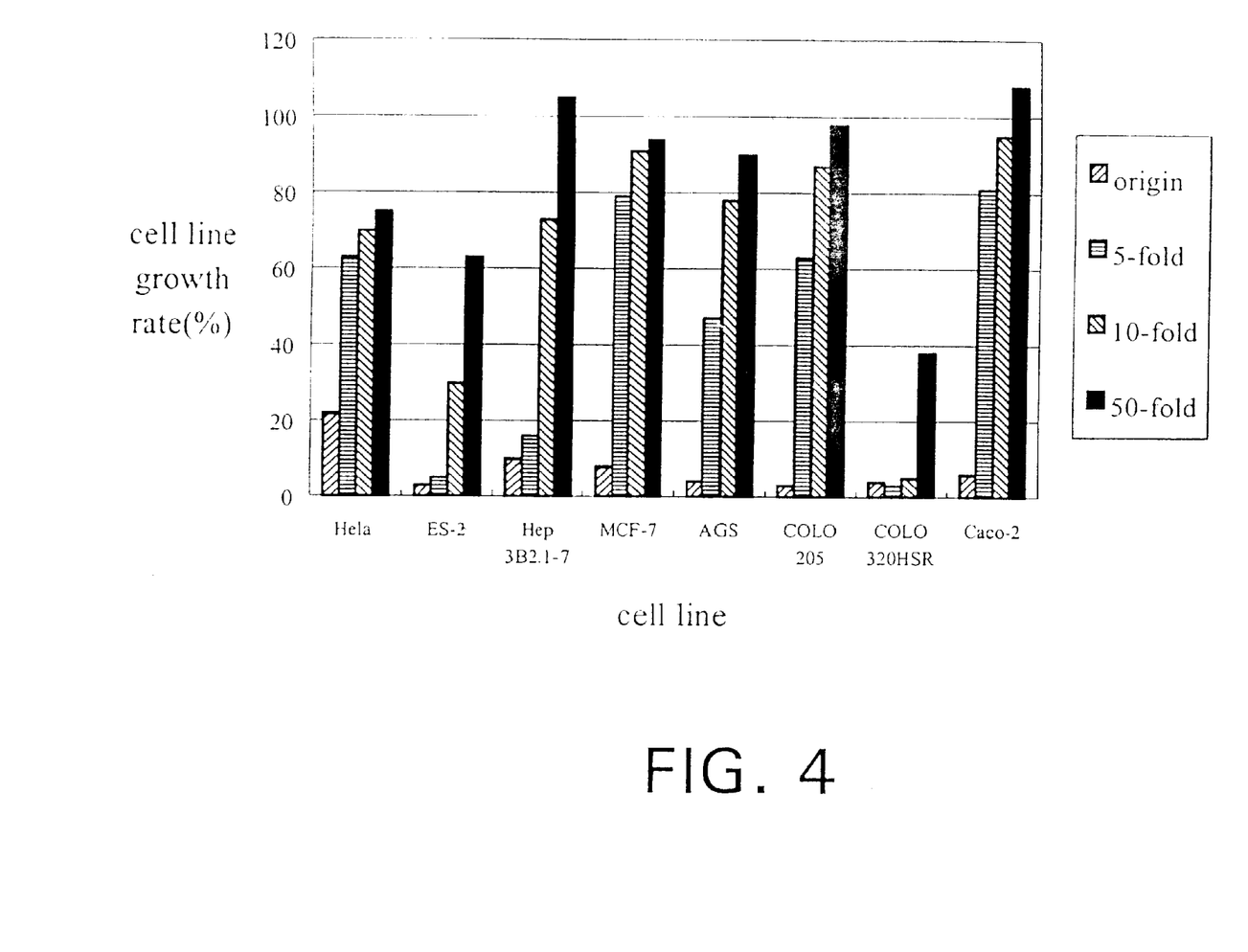
FIG. 4 is a diagram demonstrating the growth of tumor cells affected by five-, ten- and twenty-fold diluted culture filtrates of *A. camphorate* CCRC 930032, in which the tested cell lines include Hela, ES-2, Hep 38, MCF-7, AGS, COLO 205, COLO 320HSR, and Caco-2 cells.

The Inhibitory Effect on the Growth of Tumor Cells by the Diluted Culture Filtrates To identify the inhibitory strength of *A. camphorate* isolate CCRC 930032 against the growth of the tumor cells, the culture filtrate produced from a culture of the microorganism in potato dextrose broth was diluted in five-, ten- and fifty-fold and was subjected to the MTT-tetrazolium assay. The result illustrated in FIG. 4 demonstrates that as the dilution fold increases, the inhibitory effect of the culture filtrate on the tumor cells decreases gradually in a dosage-dependent manner. Nevertheless, significant inhibition to the growth of Hep 3B, AGS, ES-2, and COLO 320HSR cell lines was observed by using the five-fold diluted filtrate. The growth rate of the ES-2 and COLO 320HSR cells treated by the 50-fold diluted filtrate were still inhibited to below forty percent, as compared to the results from the non-treated cells.

EXAMPLE 6

Figure 5:
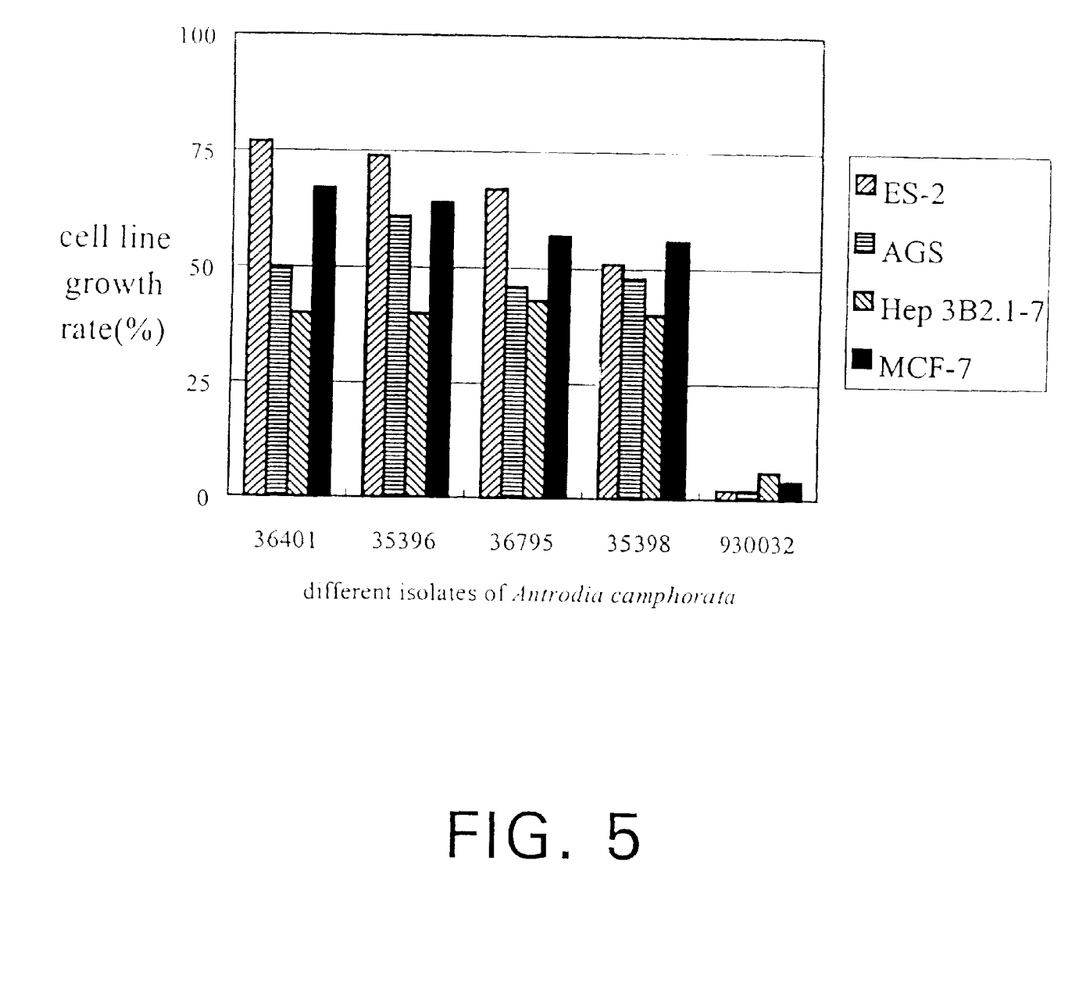
FIG. 5 is a diagram demonstrating the growth of tumor cells affected by the shake culture filtrates derived from five isolates of *A. camphorate*, i.e. CCRC 35396, 35398, 36401, 36795 and CCRC 36799, in which the tested cell lines include ES-2, AGS, Hep 3B2.1-7, and MCF-7 cells.

Inhibitory effects of the cultures of different isolates of *A. camphorata* upon tumor cells Examples 1 and 3 were repeated except that the *A. Camphorata* isolate CCRC 930032 was replaced with four other isolates, CCRC 35396, 35398, 36401 and 36795, respectively. At the end of incubation, the filtrates derived from the four isolates all appear yellow in color. As illustrated in FIG. 5, the results reveal that isolate CCRC 930032 is superior to the other four isolates in terms of the activity in inhibiting the growth of the tested tumor cells. *A. camphorata* isolate CCRC 930032 thus appears to be a promising candidate for the manufacture of a pharmaceutical composition or a nutrient supplement.

While the invention has been described with reference to the above specific embodiments, it should be recognized that various modifications and changes which will be apparent to those skilled in the relevant art, may be made without departing from the spirit and scope of the invention.

We claim:

1. A process for producing a culture of *A. camphorata* having pharmacological activity, comprising:
   (a) inoculating a mycelial inoculum of an isolate of *A. camphorata* into a medium suitable for the growth of said isolate;
   (b) cultivating the resulting culture from step (a); and
   (c) harvesting the culture when the culture has a redness index $a \geq 7$ as measured using Hunter's coordinate system.

2. The process of claim 1, wherein the isolate used in the inoculation step (a) is an isolate of *A. camphorata* deposited in Food Industry Research and Development Institute (FIRDI) with an accession number CCRC 930032 and in American Type Culture Center (ATCC) with an accession number PTA-1233.

3. The process of claim 1, wherein the medium is selected from potato dextrose broth, or a synthetic medium containing fructose as a major carbon source.

4. The process of claim 3, wherein the synthetic medium contains yeast extract as the nitrogen source.

5. The process of claim 3, wherein the synthetic medium optionally contains malt extract or glucose.

6. The process of claim 1, wherein the pharmacological activity is an inhibitory activity against tumor or cancer cells.

* * * * *